(12) United States Patent
Soluri et al.

(10) Patent No.: US 9,408,583 B2
(45) Date of Patent: Aug. 9, 2016

(54) PORTABLE GAMMA CAMERA

(71) Applicant: CONSIGLIO NAZIONALE DELLE RICERCHE (CNR), Rome (IT)

(72) Inventors: Alessandro Soluri, Rome (IT); Roberto Massari, Rome (IT)

(73) Assignee: CONSIGLIO NAZIONALE DELLE RICERCHE (CNR), Rome (IT)

( * ) Notice: Subject to any disclaimer, the term of this patent is extended or adjusted under 35 U.S.C. 154(b) by 0 days.

(21) Appl. No.: 14/435,893

(22) PCT Filed: Oct. 15, 2013

(86) PCT No.: PCT/IT2013/000285
§ 371 (c)(1),
(2) Date: Apr. 15, 2015

(87) PCT Pub. No.: WO2014/061047
PCT Pub. Date: Apr. 24, 2014

(65) Prior Publication Data
US 2015/0282773 A1    Oct. 8, 2015

(30) Foreign Application Priority Data

Oct. 16, 2012   (IT) .............................. RM2012A0491

(51) Int. Cl.
| G01T 1/164 | (2006.01) |
| A61B 6/00 | (2006.01) |
| A61B 6/06 | (2006.01) |
| A61B 6/10 | (2006.01) |
| H04N 5/225 | (2006.01) |

(52) U.S. Cl.
CPC ................ *A61B 6/4258* (2013.01); *A61B 6/06* (2013.01); *A61B 6/107* (2013.01); *A61B 6/4291* (2013.01); *A61B 6/4405* (2013.01); *A61B 6/508* (2013.01); *H04N 5/2252* (2013.01)

(58) Field of Classification Search
CPC ... G01T 1/2985; G01T 1/1642; G01T 1/1644; G01T 1/202; G01T 1/172
See application file for complete search history.

(56) References Cited

U.S. PATENT DOCUMENTS

| 6,388,258 | B1 * | 5/2002 | Berlad et al. ............. 250/363.07 |
| 8,450,694 | B2 * | 5/2013 | Baviera et al. ........... 250/363.04 |
| 2007/0152161 | A1 * | 7/2007 | Olcott et al. ............. 250/363.07 |
| 2008/0062141 | A1 * | 3/2008 | Chandhri ..................... 345/173 |
| 2010/0090120 | A1 | 4/2010 | Soluri et al. |
| 2011/0208049 | A1 * | 8/2011 | Tumer .......................... 600/436 |
| 2013/0320212 | A1 * | 12/2013 | Valentino et al. .......... 250/336.1 |

FOREIGN PATENT DOCUMENTS

| EP | 1 967 868 A2 | 9/2008 |
| WO | 98/48300 A2 | 10/1998 |

OTHER PUBLICATIONS

International Search Report, dated Feb. 4, 2014, from corresponding PCT application.

* cited by examiner

*Primary Examiner* — David Porta
*Assistant Examiner* — Mamadou Faye
(74) *Attorney, Agent, or Firm* — Young & Thompson

(57) ABSTRACT

A portable gamma camera includes a containment body (2), a scintillation measuring structure (3) housed in the containment body (2), a collimator (4) associated with the measuring structure (3), a display (5) positioned on the containment body (2) and an electronic controller unit (6), operating between the measuring structure (3) and the display (5) for generating on the display (5) images representing the radiation intercepted by the measuring structure (3).

11 Claims, 4 Drawing Sheets

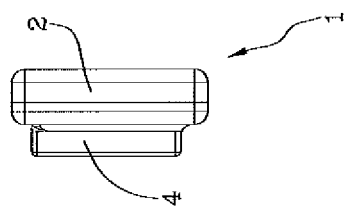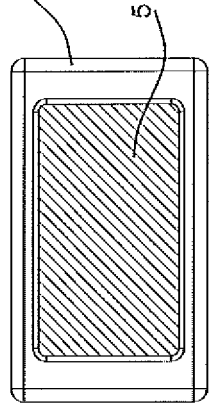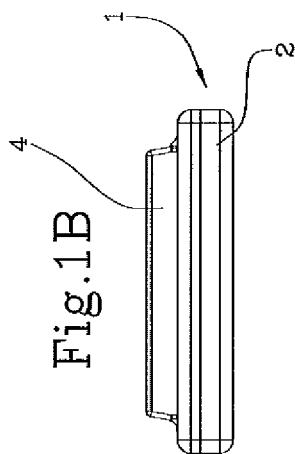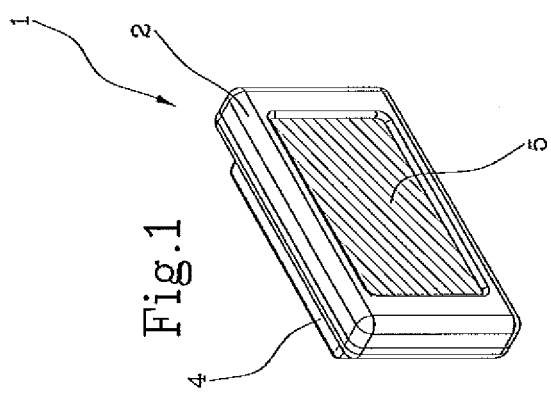

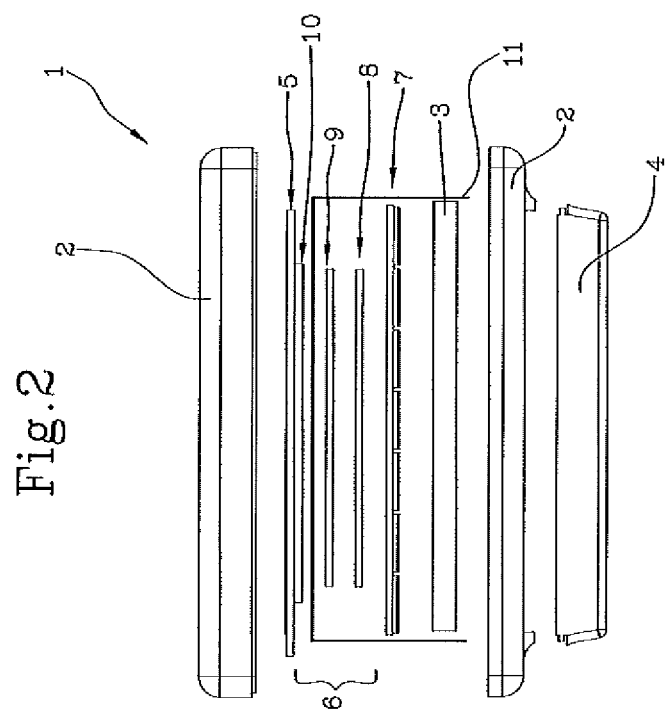
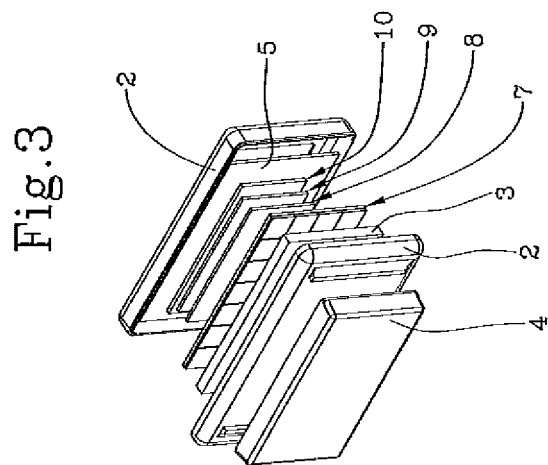

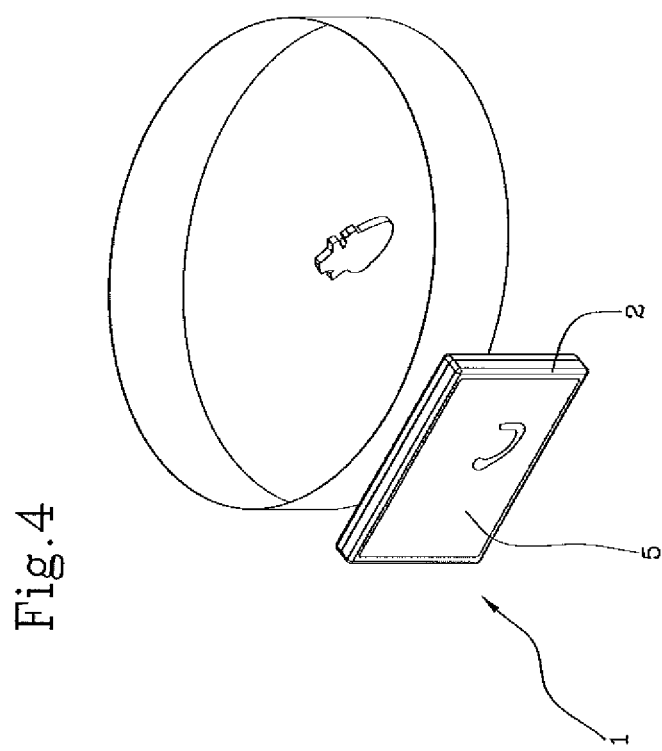

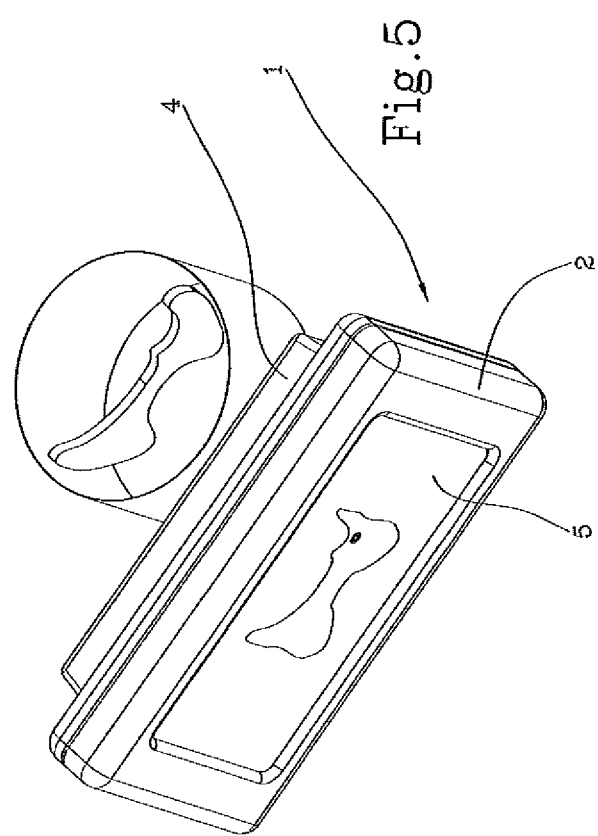

PORTABLE GAMMA CAMERA

TECHNICAL FIELD

This invention relates to a portable gamma camera, in particular of the fully integrated type, that is to say, designed to operate without any cable for external connection with other apparatuses.

The main field of use of the device is oriented towards medico-diagnostic applications.

BACKGROUND ART

It is known that in the medical diagnostic applications there is frequently a need for portable instruments which are easy to handle, in such a way as to allow a direct use of the instrument (detector) on the patient and a display of the images with dedicated units positioned close to the detector. These type of detectors are characterised by a limited measuring area and a relatively light weight.

This type of application finds a technical justification linked to the fact that the overall weight of the detector may only be reduced by reducing the measuring area and consequently the use of portable detectors may find a valid use, for example, in operating rooms and in radioguided surgery, as well as in the diagnosis of small organs. The separation between detector and control/display unit is often necessary to reduce the weight of the entire detector, since otherwise it would not be easy to handle in use.

Typically, the weight of these detectors is due mainly to the materials for shielding against external radiation (shielding of the scintillation structure and collimator) which must not reach the measuring surface and typically the weight is about 1-2 kg for the most advanced detectors, having a small measuring area (5 cm×5 cm). Clearly, the component linked to the use of the electronic equipment also affects the final dimensions and, consequently, the actual possibility of making the detector made in this way easy to handle.

Therefore, the above-mentioned portable detectors prevent the display of the images directly on the same structure handled by the operator. A small device, having a small area and which can be easily handled, may be positioned directly on the organ in question, which is extremely difficult to achieve with a large detector. Reducing the organ-detector distance also has a considerable affect on the spatial resolution of the devices for diagnostic purposes.

In common practice, the use of large detectors sometimes allows for adjustments to the organ-detector position, to be performed only after some preliminary acquisitions and forcing the operator to make successive positionings of the detector on the area to be analysed. In practice, the need to separate the measuring units from the control and display unit, even if only limited to systems with large areas, finds a logic in the type of investigation in which the detector is much larger than the organ of the patient to be analysed whilst, on the other hand, it is extremely critical when the measuring area is small compared with the area where the detector is to be positioned to search for any diseases and which therefore needs rapid successive explorations. The advantage in the operating room appears very evident where the exploration of areas of tissue with a small detector necessarily needs preliminary measurements for the correct positioning of the measuring area on the part in question or on the organ (colon, breast, thyroid and parathyroids, etc.)

In the case of detectors with small areas, where the detector is, in any case, separated from the control and display unit, for obvious reasons of reducing the weight of the entire device, the need to position the detector with respect to the physical area to be investigated results in the need for the operator to identify diagnostic details of the image observed on an external monitor, far from the corresponding investigation area, with the consequent need to apply inevitable approximations with respect to that which is displayed, not having an immediate correspondence between the physical area of the display and that of the detector.

A portable measuring instrument is also known, from the United States patent US2011/0208049, which has a display screen integrated in the detector itself.

However, this instrument has measuring elements (made from semiconductors, in particular CdZnTe) with very large dimensions (3 mm×3 mm) which considerably penalise the achievement of acceptable spatial resolutions.

More specifically, patent US2011/0208049 indicates a total investigation area (for the system known as "Microimager") which ranges from 3 inches×3 inches up to 5 inches×5 inches. Developing these measuring areas, the minimum number of measuring elements for the smallest device, using 3 mm×3 mm pixels, would be 625. Every element of CdZnTe is connected with a single pre-amplifier using a series of ASIC chips known as "RENA", each of which can control up to a maximum of 32 signals. In practice, at least twenty RENA chips would be required to control all the signals necessary for the operation of the gamma camera. Considering the dimensions of these chips, which are commercially produced in the updated version of 36 simultaneous signals per single chip, the volume necessary for packaging the chips and their control card appears very high and not easily suited to the desired characteristics of compactness and ease of handling. Moreover, since every pre-amplifier develops an absorption of at least 5 mW per channel, as indicated by the latest model produced, the total consumption would be equal to at least 3 W. Moreover, in order to control 32-36 signals, each RENA chip is combined with a single ADC (analogue-digital converter) with an average consumption of approximately 100 mW. Consequently, 20 RENA chips require at least as many ADCs, with a resulting average consumption of at least another 2 W. The development of the RENA-3 cards results in an integrated card with 4 RENA chips mounted on board for simultaneously controlling 4 blocks with 4 ADCs, for a total of 144 channels. Each ADC is linked to the use of a FPGA, the average consumption of which may be estimated to be approximately 0.5 W. Consequently, the consumption linked to the use of 5 cards with 4 RENA chips on board is approximately at least 2.5 W. The total estimated for these electronics is therefore 7.5 W, without considering the other consumptions linked to other components (display, microprocessor, etc.).

In order to operate the 625 elements at least 5 complete cards of ADCs would be needed. The dimensions of the single RENA card with 4 integrated chips is approximately 20 cm×6 cm, with a thickness of at least 1-2 cm linked to the presence of components and connectors and the necessary presence of cooling fans for dissipating heat, required to reduce the temperature linked to the use of a multitude of cards which dissipate heat. In that situation, the absorption linked to the electronics for controlling the signals, without considering other consumptions, is very high (approx. 7-8 W) as well as certainly not providing small dimensions. In effect, the minimum area necessary to house the cards must be at least 20 cm×at least 6 cm, in addition to the positioning of the detector, the smallest dimension of which is approximately 7.5 cm×7.5 cm (3 inches×3 inches). For this reason, the dimensions of the outer container may not be less than 20 cm×10 cm×12-15 cm. The problems of high total absorption (approx. 8 W) and the total volume developed by the electronics required for the operation make it not very practical to achieve a device which is easy to handle (that is, compact and light). All of this with a total weight closely linked to the use of a collimator suitable for the diagnostic use. For a standard 24 mm collimator made of lead which can be adapted to the measuring area (7.5 cm×7.5 cm) and 2 mm holes, with 2 mm lead rings for cutting the non-parallel events which cross the partitions, a weight of not less than 600 grams may be assumed, to which it is necessary to add the 2 mm lateral shielding again made of lead for the measuring elements as well as the weight of the batteries necessary to operate the apparatus (with the above-mentioned consumptions very high) at least for a duration of 2 hours. Consequently, the weight of the device can easily exceed 2 kg and an estimated volume of 20 cm×10 cm×15 cm. From the data given in the above-mentioned patent, the absorption characteristics of the RENA cards, the number of which is strongly dependent on the number of CdZnTe pixels, are compatible with a total value of at least 8 W.

In the case of a larger area, as indicated in the text of the patent (and in particular in the case of a total measuring area of 5 inches×5 inches), 42×42 CdZnTe elements would be needed (a total of 1764 elements). The control of these elements requires 49 chips, if the new 36-channel RENA-3 is used. At least 11 cards would be necessary, fitted with a 4-channel ADC, if 4 RENA chips are mounted on each board. It would therefore be necessary to supply 1764 elements which absorb at least 5 mW each, bringing the absorption to approximately 9 W. The 49 cards with ADC on board would develop at least 5 W, whilst the absorption of the 11 cards with FPGA would consume another 5.5 W. It would all consume approximately 20 W and would have a total size of 20 cm×20 cm×15 cm.

Comparing the ratio between measuring area and overall volume, it may be considered that in the case of the above-mentioned patent, for the development of a measuring area of 3 inches×3 inches this value is approximately 1.9%, whilst in the case of a measuring area of 5 inches×5 inches this value is 2.7%

With reference to the performances which can be obtained, it is necessary to consider that the attempt to improve the spatial resolution in this type of detector would require reducing the size of the measuring elements and, consequently, increasing the number of pre-amplification channels of the RENA chips and of the ADCs. By way of an example, in order to reach a nominal intrinsic resolution of approximately 1 mm, the area of 3 inches×3 inches should have 5776 CdZnTe elements, so more than 160 RENA chips and more than 40 ADCs. This would all lead to a height of the detector of more than 80 cm, which clearly cannot be proposed as a technical solution. Moreover, the consumption in terms of absorption (65 W) would be extremely high for a small range device.

Similarly, the attempt to improve the ease of handling in this type of detector, which would therefore require reducing weights and dimensions of the detector, can only lead to the reduction of the electronics installed and therefore the reduction of the number of CdZnTe measuring elements. This, for the same total measuring area, considerably penalises the spatial resolution which can be obtained.

Thus, starting from the detector described in patent US2011/0208049, every attempt to improve the ease of handling of the detector would lead to a significant worsening of the spatial resolution whilst, on the other hand, every attempt to improve the spatial resolution of the detector would lead to a significant worsening of the ease of handling.

In other words, the teachings of US2011/0208049 make the size and consumption characteristics, which are fundamental elements for making a device compact and easy to handle, strongly dependent on the real spatial resolution dimensions which can be obtained. In order to reach acceptable resolution values this technology requires the use of particular electronic cards which are necessarily voluminous with respect to the requested performance and the total consumption of which also affects significantly the final weight (increase in the number of batteries, total weight of the system). It is evident that a device for which its volume increases due to the length necessary to achieve the optimum resolution does not represent a solution to the problem of making a device which is truly easy to handle, compact and light in weight.

DISCLOSURE OF THE INVENTION

The aim of this invention is therefore to provide a portable gamma camera having an optimum spatial resolution and, at the same time, distinctly miniaturizable (more specifically, having a low weight and compact dimensions, and therefore being very easy to handle).

BRIEF DESCRIPTION OF DRAWINGS

This aim is fully achieved by the portable gamma camera according to this invention as characterised in the appended claims.

The technical features of the invention, with reference to the above aim, are clearly described in the claims below and its advantages are apparent from the detailed description which follows, with reference to the accompanying drawings which illustrate a preferred, non-limiting example embodiment of the invention, and in which:

FIG. 1 is a schematic perspective view of a portable gamma camera according to this invention;

FIGS. 1A-1C are three views at right angles of the gamma camera of FIG. 1;

FIGS. 2 and 3 are two different exploded views of the gamma camera of FIG. 1;

FIGS. 4 and 5 show the gamma camera of FIG. 1 in two operational configurations.

FIGS. 1, 1A-1C and 2-3 show the constructional architecture of the gamma camera 1 according to this invention.

DETAILED DESCRIPTION OF THE PREFERRED EMBODIMENTS OF THE INVENTION

More specifically, the gamma camera 1 comprises a containment body 2, which is box-shaped and easy to handle by a user, which houses inside a measuring structure 3 (visible in FIGS. 2 and 3) designed to receive a radiation, in particular a gamma type radiation.

The expression "easy to handle" means a containment body 2 having a configuration (shape, dimensions) so as to be easily handled manually by an operator. For example, in a preferred embodiment the containment body 2 has a substantially parallelepiped shape having dimensions similar to a compact photographic camera, for example 12 cm×10 cm×3 cm (without collimator).

Preferably, the containment body 2 is coated with a shielding shell, made for example from lead (Pb) tungsten (W), tantalum, etc.

With reference to the measuring structure 3, it is advantageously made of of the scintillation type. In an embodiment it comprises a matrix of scintillation crystals which are able to convert photons of energy of between 20 keV and 1 MeV (for example CsI(Tl), NaI(Tl), LaBr$_3$(Ce), ClBr$_3$(Ce)). In a different embodiment, the measuring structure 3 comprises a single planar crystal made from the same material mentioned above.

On the containment body 2 there is a collimator 4 made of a material with a high atomic number (for example lead, tungsten, tantalum), associated with the measuring structure 3 for absorbing a lateral radiation directed towards the measuring structure 3 and having an angle of incidence greater than a predetermined value. The collimator 4 can be fixed or interchangeable with a collimator of a different length.

From the structural point of view, the collimator 4 is of substantially known type and defined by a matrix of parallel channels subdivided by separating partitions. Preferably, the collimator 4 has a length of between 12 mm and 52 mm.

On the containment body 2, and more specifically on the side opposite the collimator 4, there is a display 5 for displaying images representing the distribution of radiation incident on the measuring structure 3 and therefore, in the case of medical diagnostics, representing the morphological-functional status of an organ or part of a patient or of a tumour.

Therefore, in this configuration, the containment body 2 (which preferably comprises two half-shells as shown in FIG. 3) extends between the collimator 4 and the display 5.

The containment body 2 also houses inside an electronic controller unit 6, interposed between the measuring structure 3 and the display 5 for generating on the display 5 images representing the radiation intercepted by the measuring structure 3.

Advantageously, the electronic controller unit 6 comprises one or more optoelectronic converters 7 with a low voltage supply (that is, with a voltage less than 100 V) having a single structure, or a matrix comprising a series of single elements, having the characteristic of reading the load which reaches them and consequently having the possibility of being positioned in a similar manner to a surface of evenly spaced anodes and able, using suitable electronics, to generate electrical signals proportional to the intensity of the interacting photons.

FIG. 3 shows an embodiment of the optoelectronic converter 7 comprising a single card having a matrix of optoelectronic conversion elements 7.

Preferably, the optoelectronic converters (7) are selected from the group comprising APD, SiPM and/or MPPC.

The electronic controller unit 6 comprises, in sequence:

A first card 8 relative to the optoelectronic converters 7, comprising an electronic system designed to perform a reading, amplification and integration of the signals generated by the optoelectronic converters, and a resistive network connected to the above-mentioned electronic reading, amplification and integration system, able to determine the load barycentre and the energy associated with the radiation which strikes the scintillation structure 3;

a second card 9 relative to the system for analogue/digital conversion and sampling of the signals using PIC (Programmable Integrated Circuit or Programmable Interface Controller) devices equipped with ADC/DAC converters, designed to receive from the resistive network a signal identifying the load barycentre and the energy associated with the radiation which strikes the scintillation structure 3 and also designed to integrate the signal for determining the amplitude and generating a respective output signal (the analogue/digital conversion system preferably comprises a miniaturised ADC with several channels which is able sample the signals for supplying the position and the energy of the scintillation event;

a PIC or ARM (Advanced RISC Machine, originally Acorn RISC Machine) type microcontroller system 10, connected to the conversion and sampling system for receiving the above-mentioned output signal and converting it into an image which can be displayed on the display 5.

In an embodiment not illustrated, the first card 8 is integrated with the optoelectronic converter 7.

Preferably, the microcontroller system 10 is directly integrated on the display 5.

In more detail, the ARM architecture indicates a family of 32-bit RISC microprocessors used in a multitude of "embedded" systems thanks to its low consumption characteristics (in ratio to its performance) suitable where the energy saving of the batteries is essential.

Moreover, the microcontroller system is designed to process the data downloaded on an auxiliary memory and in such a way that the data can be processed by suitable software for displaying images on the display 5 in a scale of false colours which can be interpreted by the users.

Alternately, instead of the above-mentioned PIC/ARM microcontroller for handling the data processing there can be a suitable control system integrated in the display which is therefore able to process a high number of events (preferably more than 100 k/second) with its own control system.

In an embodiment illustrated in FIG. 2, the scintillation structure 3 and the optoelectronic converter 7 are enclosed, together with the above-mentioned first and second card 8, 9, inside a case 11 made of a material with a high atomic number (for example Pb) designed to contain the diffusion of gamma radiation, in particular towards the display 5 in order to protect the display 5.

The case 11 is open at the front, towards the collimator 4, so as not to interfere with the gamma radiation coming from the outside and directed towards the scintillation matrix 3.

In a different embodiment (not illustrated), the case 11 encloses the scintillation structure 3 and the optoelectronic converter 7 but not the above-mentioned first and second cards 8, 9.

Lastly, the containment body 2 houses inside a rechargeable battery which is able to power all the electronic components, the display 5 and the microprocessor for guaranteeing an adequate duration, for example, for the clinical use.

In a different embodiment, the gamma camera 1 is powered by connecting to the mains supply by cable. In that solution, the battery could be omitted.

In other words, therefore, electronic controller unit 6, the rechargeable battery (where provided) and the scintillation structure 3 are contained entirely in the containment body 2.

The use of the above-mentioned electronic controller unit 6 therefore allows a very low level of total energy absorption to be obtained, bringing it to values of less than 1 W.

Moreover, the high degree of miniaturization of the components constituting the electronic controller unit 6 and the small size of the battery, optimised for extremely low energy absorption, allow a marked reduction in the dimensions of the containment body 2, whilst maintaining a large measuring area.

More specifically, the containment body 2 has a ratio between measuring area (that is, the active area of the measuring structure 3) and volume greater than 0.10 and preferably greater than 0.20. This value can reasonably be contained within the range 0.10-0.50.

In an embodiment, the scintillation structure 3 has a measuring area of approximately 8 cm×8 cm (64 cm$^2$) whilst the containment body 2 has external dimensions which are entirely inscribable in a parallelepiped having dimensions of approximately 10 cm×10 cm×3 cm (volume of approximately 300 cm³), with a ratio between measuring area and volume of approximately 0.21.

The above-mentioned miniaturization also allows a containment of the weight, which is advantageously less than 1.5 Kg.

Advantageously, the dimensions and the volume are independent of the number of pixels (crystals of the scintillation matrix) used, since, unlike prior art semiconductor solutions, the architecture of the gamma camera 1 according to this invention uses an electronics which does not require upgrading if the number of pixels is to be increased (for example, reducing the dimensions to increase the resolution).

More specifically, the electronic controller unit 6 uses an analogue/digital conversion system for sampling the signals which always uses four channels irrespective of the number of pixels used.

It is evident that this allows, therefore, an increase in the spatial resolution without penalising the size and ease of handling.

According to an advantageous aspect of the invention, the display 5 has a measuring area with dimensions coinciding with the measuring area of the scintillation structure 3, that is to say, with a 1:1 ratio.

Preferably, the measuring area of the display 5 has sides with different lengths and preferably with a ratio of 16:9 or 4:3.

The possibility of displaying the image with a 1:1 ratio between the area of the display 5 and the measuring area assumes an importance linked to a better identification and understanding of the diseases which can be directly observed during acquisition and without any scale reduction factor.

FIGS. 4 and 5 show two situations for diagnostic use of the gamma camera 1 wherein the heart and the thyroid of a patient are analysed, respectively.

Moreover, the use of representative solutions with 16:9 or 4:3 ratio between the sides of the detector allow a specific design optimisation linked to the use of standard and widespread components (LCD screens or the like) for the analysis of organs which, normally, have an elongate shape or which enter better in the field of view of a detector with these dimensional proportions. If, for example, a 16:9 ratio is used with the dimension of the long side being 40 cm, the short side of the area of the detector would be 22 cm. With a detector of this type, it is possible to investigate the majority of organs and make the apparatus less bulky since, for the same diagnostic investigation, a detector with square dimensions would have a large portion of the measuring area unused. If, for example, the kidney, of elongate shape, is taken into consideration, it is possible to perform the scintigraphic analysis adapting the longest side of the detector in the direction of the longest axis of the organ, establishing in this way a use in contact with the patient having a smaller overall size of the entire apparatus. In general, all the organs have an ellipsoid shape (brain, kidney, heart, thyroid, etc.), therefore having two axes of different length.

The invention achieves the aims set by overcoming the above-mentioned disadvantages of the prior art.

More specifically, the adoption of a scintillation measuring system allows the adoption of a low absorption electronic controller unit and distinctly miniaturizable which can be inserted in a single container without using cables connecting with external output apparatuses, but, on the contrary, fitting the entire operating unit in a single machine body, equipped with a display positioned behind the detector, so as to guarantee a correct display of the information produced.

The electronic controller unit used is also able to always use, in association with the resistive network used, four signal sampling channels irrespective of the number of pixels used, and this makes it possible to increase the spatial resolution without penalising the dimensions and the ease of handling.

Moreover, the absorption of the calculation systems can be reduced by using suitable processing systems with reduced calculation output thanks to the particular operational logic of the electronic controller unit used which does not require a significant increase in the calculation output with the increase of the desired spatial resolution or the measuring area.

The resulting structure of the gamma camera according to this invention is therefore compact and easy to handle.

More specifically, the compactness requirement is satisfied by the ratio between the measuring area and volume of the containment body, greater than 0.10 and up to 0.50 and above. The easy to handle requirement is, on the other hand, satisfied by the small dimensions and by the low weight, which make the gamma camera easy to manoeuvre manually by the operator without the need for auxiliary supports and without exercising particular physical efforts.

This makes the gamma camera according to this invention suitable for the localisation of diseases in operating rooms and for the diagnostic investigation of small organs, as well as the scintigraphic analysis of organs of small animals, so as to trial new radio-marked antibodies, which are specific for certain diseases. Moreover, its application can be planned in safety sectors (airports) or for industrial diagnostics. The main use of the gamma camera relates to the localisation of tumoral lesions, especially in those techniques which require an adequate spatial precision such as biopsies (prostate and breast) or in radioguided or radioimmunoguided surgical operations or as a monitoring system in radiometabolic therapy, radioguided surgery and radiant therapy techniques.

This gamma camera can be effectively applied in many diagnostic techniques where the fast display of the diagnostic details and their relative position relative to the image produced provides the user with an array of information useful in the continuation of the clinical procedures. For example, the localisation of thyroid nodules, diseases linked to bone inflammations (diabetic feet) and sentinel lymph nodes are all techniques which can be quickly localised with a device positioned directly on the cutis of the patient.

The invention claimed is:

1. A portable gamma camera, comprising:
    a containment body;
        a measuring structure housed inside the containment body and designed to receive radiation;
        a collimator made of a material with a high atomic number, associated with the measuring structure for absorbing a lateral radiation directed towards the measuring structure and having an angle of incidence greater than a predetermined value;
        a display, positioned on the containment body;
        an electronic controller unit, operating between the measuring structure and the display for generating on the display images representing the radiation intercepted by the measuring structure;
    wherein the measuring structure comprises a scintillation structure,
    wherein the electronic controller unit comprises at least one optoelectronic converter selected from the group comprising APD, SiPM and/or MPP,
    wherein the electronic controller unit also comprises:
        an electronic system designed for reading, amplifying and integrating output signals from the optoelectronic converters;

a resistive network connected to the electronic system and able to determine the load barycentre and the energy associated with the radiation which strikes the scintillation structure;

a system for analogue/digital conversion and sampling of the signals using PIC devices equipped with ADC/DAC, the conversion and sampling system being designed to receive from the resistive network a signal identifying the load barycentre and the energy associated with the radiation which strikes the scintillation structure and being designed to integrate the signal for determining the amplitude and generating a respective output signal;

a PIC or ARM type microcontroller system, connected to the conversion and sampling system for receiving the output signal and converting it into an image which can be displayed on the display;

wherein the electronic system designed for reading, amplifying and integrating, the resistive network, the analogue/digital conversion system and the microcontroller system are positioned sequentially between the opto-electronic converter and the display, and wherein the containment body houses inside a rechargeable battery which is able to power all the electronic components, the display and the microprocessor for guaranteeing an adequate duration, the electronic controller unit having a level of total energy absorption lower than 1 W.

2. The gamma camera according to claim 1, wherein the display has a display area having dimensions coinciding with the measuring area of the scintillation structure.

3. The gamma camera according to claim 2, wherein the display area has sides with different lengths.

4. The gamma camera according to claim 1, wherein the containment body comprises two half-shells and extends between the collimator and the display and contains entirely the electronic controller unit.

5. The gamma camera according to claim 1, wherein the containment body has a ratio between measuring surfaces and volume greater than 0.10.

6. The gamma camera according to claim 5, wherein the scintillation structure has a measuring area of not less than 10 $cm^2$.

7. The gamma camera according to claim 1, wherein the containment body is at least partly made, with a material screening against gamma radiation.

8. The gamma camera according to claim 1, wherein the scintillation structure comprises a matrix of scintillation crystals which are able to convert photons of energy of between 20 keV and 1 MeV.

9. The gamma camera according to claim 2, wherein the display area has sides with different lengths with a ratio of 16:9 or 4:3.

10. The gamma camera according to claim 1, wherein the containment body has a ratio between measuring surfaces and volume greater than 0.20.

11. The gamma camera according to claim 1, wherein the containment body is coated with a material screening against gamma radiation.

* * * * *